(12) United States Patent
Domb et al.

(10) Patent No.: US 8,221,442 B2
(45) Date of Patent: Jul. 17, 2012

(54) DEVICE SYSTEM AND METHOD FOR TISSUE DISPLACEMENT OR SEPARATION

(75) Inventors: Abraham Jackob Domb, Efrat (IL); Shaul Shohat, Kfar HaOranim (IL)

(73) Assignee: Bioprotect Ltd., Kfar-Saba (IL)

( * ) Notice: Subject to any disclaimer, the term of this patent is extended or adjusted under 35 U.S.C. 154(b) by 1093 days.

(21) Appl. No.: 11/630,257

(22) PCT Filed: Jun. 23, 2005

(86) PCT No.: PCT/IL2005/000672
§ 371 (c)(1), (2), (4) Date: Dec. 21, 2006

(87) PCT Pub. No.: WO2006/001009
PCT Pub. Date: Jan. 5, 2006

(65) Prior Publication Data
US 2008/0033471 A1    Feb. 7, 2008

Related U.S. Application Data

(60) Provisional application No. 60/581,769, filed on Jun. 23, 2004.

(51) Int. Cl.
*A61M 29/00*    (2006.01)
(52) U.S. Cl. .................................................. 606/192
(58) Field of Classification Search .................. 606/191, 606/192, 193, 194, 195, 199; 128/843
See application file for complete search history.

(56) References Cited

U.S. PATENT DOCUMENTS

| | | | |
|---|---|---|---|
| 4,513,058 A * | 4/1985 | Martin | 428/336 |
| 5,318,586 A | 6/1994 | Ereren et al. | |
| 5,334,210 A | 8/1994 | Gianturco et al. | |
| 5,336,252 A | 8/1994 | Cohen | |
| 5,458,612 A | 10/1995 | Chin | |
| 5,516,522 A | 5/1996 | Peyman et al. | |
| 5,641,505 A | 6/1997 | Bowald et al. | |
| 5,653,758 A | 8/1997 | Daniels et al. | |
| 5,720,762 A | 2/1998 | Bass | |
| 6,019,781 A | 2/2000 | Worland | |
| 6,102,928 A | 8/2000 | Bonutti | |
| 6,187,023 B1 | 2/2001 | Bonutti | |
| 6,248,131 B1 | 6/2001 | Felt et al. | |

(Continued)

FOREIGN PATENT DOCUMENTS

DE    102007018341    10/2008

(Continued)

OTHER PUBLICATIONS

Communication Relating to the Results of the Partial International Search Dated Nov. 18, 2005 From the International Searching Authority Re.: Application No. PCT/IL2005/000672.

(Continued)

*Primary Examiner* — Ryan Severson
*Assistant Examiner* — Tin Nguyen

(57) ABSTRACT

A tissue displacement/separation device is provided. The device includes a bladder which is expandable between a first tissue and a second tissue of a body. The bladder has an expanded shape which is selected capable of displacing or separating the first tissue from the second tissue in a manner suitable for protecting the first tissue from an effect of a treatment applied to the second tissue.

14 Claims, 9 Drawing Sheets

U.S. PATENT DOCUMENTS

| | | | |
|---|---|---|---|
| 6,527,693 B2 | 3/2003 | Munro, III et al. | |
| 6,746,465 B2 | 6/2004 | Diederich et al. | |
| 6,932,834 B2 | 8/2005 | Lizardi et al. | |
| 7,144,398 B2 | 12/2006 | Chern Lin et al. | |
| 7,404,791 B2 | 7/2008 | Linares et al. | |
| 7,601,113 B2 | 10/2009 | Lebovic et al. | |
| 2002/0052653 A1 | 5/2002 | Durgin | |
| 2002/0058947 A1 | 5/2002 | Hochschuler et al. | |
| 2003/0028196 A1* | 2/2003 | Bonutti | 606/87 |
| 2003/0036728 A1 | 2/2003 | Samson et al. | |
| 2003/0105469 A1 | 6/2003 | Karmon | |
| 2003/0181939 A1 | 9/2003 | Bonutti | |
| 2004/0038874 A1 | 2/2004 | Omoigui | |
| 2004/0097794 A1 | 5/2004 | Bonutti | |
| 2004/0143285 A1 | 7/2004 | Bonutti | |
| 2004/0254625 A1 | 12/2004 | Stephens et al. | |
| 2004/0267315 A1 | 12/2004 | Wolf et al. | |
| 2005/0245938 A1 | 11/2005 | Kochan | |
| 2005/0273075 A1 | 12/2005 | Krulevitch et al. | |
| 2005/0278025 A1 | 12/2005 | Ku et al. | |
| 2006/0100629 A1 | 5/2006 | Lee | |
| 2006/0106361 A1 | 5/2006 | Muni et al. | |
| 2006/0147492 A1 | 7/2006 | Hunter et al. | |
| 2006/0149380 A1 | 7/2006 | Lotz et al. | |
| 2006/0182780 A1 | 8/2006 | Riley et al. | |
| 2006/0233852 A1 | 10/2006 | Milbocker | |
| 2006/0241766 A1 | 10/2006 | Felton et al. | |
| 2007/0038292 A1 | 2/2007 | Danielpour | |
| 2007/0078477 A1 | 4/2007 | Heneveld, Sr. et al. | |
| 2007/0118218 A1 | 5/2007 | Hooper | |
| 2007/0198022 A1 | 8/2007 | Lang et al. | |
| 2008/0269897 A1 | 10/2008 | Joshi et al. | |
| 2009/0112214 A1 | 4/2009 | Philippon et al. | |
| 2010/0023127 A1 | 1/2010 | Shohat | |
| 2010/0069947 A1 | 3/2010 | Sholev et al. | |
| 2011/0295226 A1 | 12/2011 | Shohat et al. | |

FOREIGN PATENT DOCUMENTS

| | | |
|---|---|---|
| DE | 102007051782 | 5/2009 |
| EP | 0507645 | 10/1992 |
| JP | 06-510450 | 11/1994 |
| JP | 2003-325685 | 11/2003 |
| JP | 2006-247257 | 9/2006 |
| WO | WO 93/04727 | 3/1993 |
| WO | WO 2006/001009 | 1/2006 |
| WO | WO 2006/055516 | 5/2006 |
| WO | WO 2006/074879 | 7/2006 |
| WO | WO 2007/002561 | 1/2007 |
| WO | WO 2007/054934 | 5/2007 |
| WO | WO 2007/125060 | 11/2007 |
| WO | WO 2008/111073 | 9/2008 |
| WO | WO 2008/111078 | 9/2008 |
| WO | WO 2008/139473 | 11/2008 |

OTHER PUBLICATIONS

International Preliminary Report on Patentability Dated Jul. 27, 2006 From the International Preliminary Examining Authority Re.: PCT/IL2005/000672.
International Search Report Dated Feb. 22, 2006 From the International Searching Authority Re.: Application No. PCT/IL2005/000672.
Translation of the Office Action Dated Oct. 31, 2008 From the State Intellectual Property Office of the People's Republic of China Re.: Application No. 200580028684.5.
Written Opinion Dated Feb. 22, 2006 From the International Searching Authority Re.: Application No. PCT/IL2005/000672.
Restriction Official Action Dated Dec. 12, 2011 From the US Patent and Trademark Office Re. U.S. Appl. No. 12/531,073.
Translation of Notice of Reason for Rejection Dated Nov. 5, 2010 From the Japanese Patent Office Re. Application No. 2007-517651.
Response Dated Dec. 30, 2011 to the Communication Pursuant to Rules 70(2) and 70a(2) EPC of Jun. 24, 2011 From the European Patent Office Re. Application No. 08738353.5.
Communication Relating to the Results of the Partial International Search Dated Nov. 3, 2011 From the International Searching Authority Re. Application No. PCT/IL2011/000637.
International Search Report and the Written Opinion Dated Jan. 9, 2012 From the International Searching Authority Re. Application No. PCT/IL2011/000637.
Response Dated Dec. 28, 2011 to Supplementary European Search Report and the European Search Opinion of Jun. 6, 2011 From the European Patent Office Re. Application No. 08738353.5.
Notification of Publication of Patent Application for Invention and Entering the Substantive Examination Proceeding Dated Jul. 28, 2010 From the Patent Office of the People's Rebublic of China Re. Application No. 200880024447.5 and Its Translation Into English.
Response Dated Oct. 20, 2010 to Notification of Publication of Patent Application for Invention and Entering the Substantive Examination Proceeding of Jul. 28, 2010 From the Patent Office of the People's Rebublic of China Re. Application No. 200880024447.5.
Notification of Publication of Patent Application for Invention and Entering the Substantive Examination Proceeding Dated Oct. 13, 2010 From the Patent Office of the People's Republic of China Re. Application No. 200880015430.3.
Response Dated Jan. 6, 2011 to Notification of Publication of Patent Application for invention and Entering the Substantive Examination Proceeding Dated Oct. 13, 2010 From the Patent Office of the People's Republic of China Re. Application No. 200880015430.3.
Translation of Office Action Dated Jan. 11, 2011 From the State Intellectual Property Office of the People's Republic of China Re. Application No. 200580028684.5.
Response Dated Feb. 27, 2011 to Office Action of Oct. 27, 2009 From the Israel Patent Office Re.: Application No. 180270.
Response Dated Apr. 21, 2011 to Notice of Reason for Rejection of Nov. 5, 2010 From the Japanese Patent Office Re. Application No. 2007-517651.
Supplementary European Search Report and the European Search Opinion Dated Jun. 6, 2011 From the European Patent Office Re. Application No. 08738353.5.
Communication Pursuant to Rules 70(2) and 70a(2) EPC Dated May 24, 2011 From the European Patent Office Re. Application No. 08738353.5.
Response Dated May 12, 2011 to Office Action of Jan. 11, 2011 From the State Intellectual Property Office of the People's Republic of China Re. Application No. 200580028684.5. & Replacement Set of (Amended) Claims.
Translation of Official Copy of Decision of Rejection Dated Jun. 7, 2011 From the Japanese Patent Office Re. Application No. 2007-517651.
Response Dated May 12, 2011 to Office Action of Jan. 11, 2011 From the State Intellectual Property Office of the People's Republic of China Re. Application No. 200580028684.5.
Invitation to Pay Additional Fees Dated Sep. 17, 2008 From the International Searching Authority Re.: Application No. PCT/IL08/00354.
Third Party Submission Under 37 CFR §1.99 Dated Mar. 26, 2010 in the US Patent and Trademark Office Re.: U.S. Appl. No. 12/531,332.
Examiner's Report Dated Apr. 28, 2010 From the Australian Government, IP Australia Re. Application No. 2005257050.
International Preliminary Report on Patentability Dated Jan. 21, 2010 From the International Bureau of WIPO Re.: Application No. PCT/IL2008/000347.
International Preliminary Report on Patentability Dated Jan. 21, 2010 From the International Bureau of WIPO Re.: Application No. PCT/IL2008/000662.
International Preliminary Report on Patentability Dated Oct. 22, 2009 From the International Bureau of WIPO Re.: Application No. PCT/IL2008/000354.
International Search Report and the Written Opinion Dated Oct. 23, 2008 From the International Searching Authority Re.: Application No. PCT/IL08/00662.
International Search Report Dated Nov. 20, 2008 From the International Searching Authority Re.: Application No. PCT/IL08/00347.
International Search Report Dated Nov. 26, 2008 From the International Searching Authority Re.: Application No. PCT/IL08/00354.
Invitation to Pay Additional Fees Dated Sep. 23, 2008 From the International Searching Authority Re.: Application No. PCT/IL08/00347.

Patentability Search on Expandable Prostheses Particularly Useful for Rotator Cuff Protection Dated Oct. 31, 2007 Effectuated by Sol Scheinbein.

Written Opinion Dated Nov. 20, 2008 From the International Searching Authority Re.: Application No. PCT/IL08/00347.

Written Opinion Dated Nov. 26, 2008 From the International Searching Authority Re.: Application No. PCT/IL08/00354.

Translation of Notice of Payment of the Restoration Fee for Unity of Invention Dated Jul. 26, 2011 From the State Intellectual Property Office of the People's Republic of China Re. Application No. 200880014369.0.

International Preliminary Report on Patentability Dated Jul. 27, 2006 From the International Preliminary Examining Authority Re.: Application No. PCT/IL2005/000672.

Translation of Office Action Dated Oct. 31, 2008 From the State Intellectual Property Office of the People's Republic of China Re.: Application No. 200580028684.5.

Office Action Dated Oct. 27, 2009 From the Israel Patent Office Re.: Application No. 180270 and Its Translation Into English.

Response Dated Jan. 4, 2010 to Decision of Rejection of Oct. 16, 2009 From the State Intellectual Property Office of the People's Republic of China Re.: Application No. 200580028684.5.

Translation of Decision on Rejection Dated Oct. 16, 2009 From the State Intellectual Property Office of the People's Republic of China Re.: Application No. 200580028684.5.

Communication Pursuant to Article 94(3) EPC Dated Dec. 1, 2011 From the European Patent Office Re. Application No. 05754685.5.

Translation of Office Action Dated Oct. 19, 2011 From the State Intellectual Property Office of the People's Republic of China Re. Application No. 200880014369.0.

\* cited by examiner

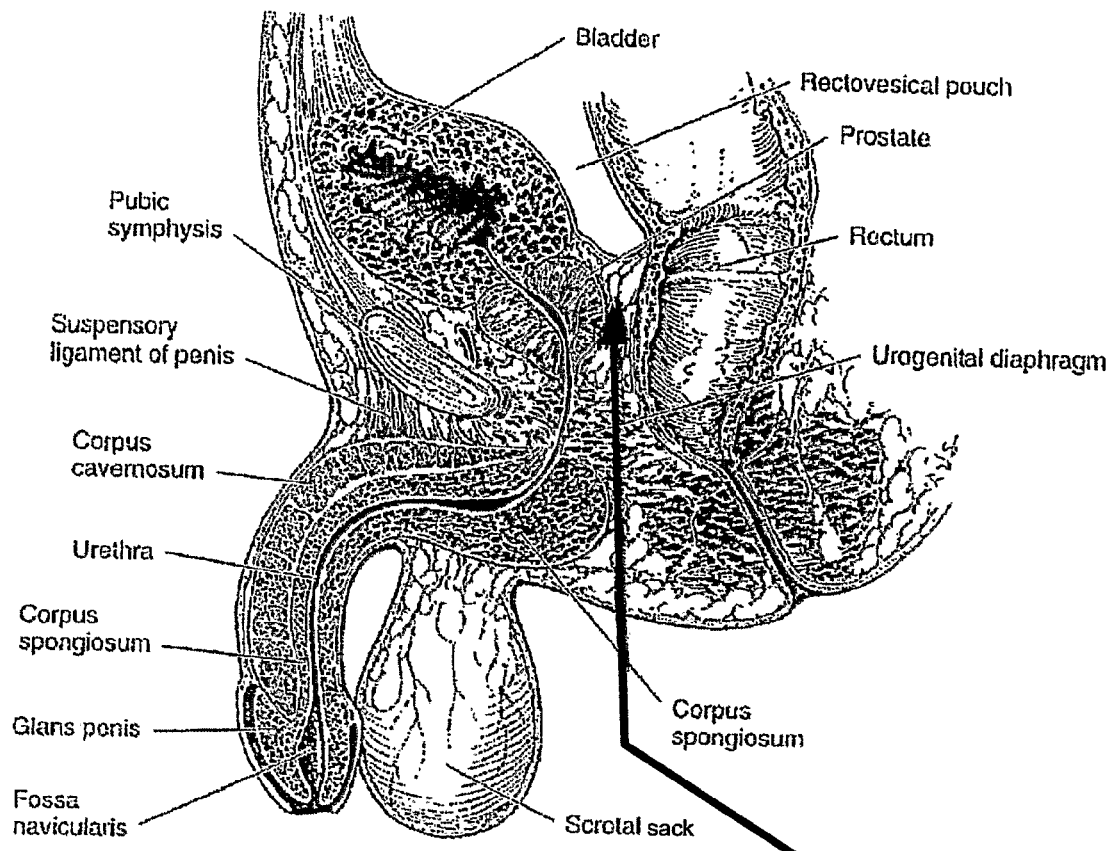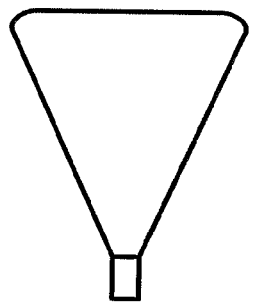
Fig. 3a
Fig. 3b    Fig. 3c

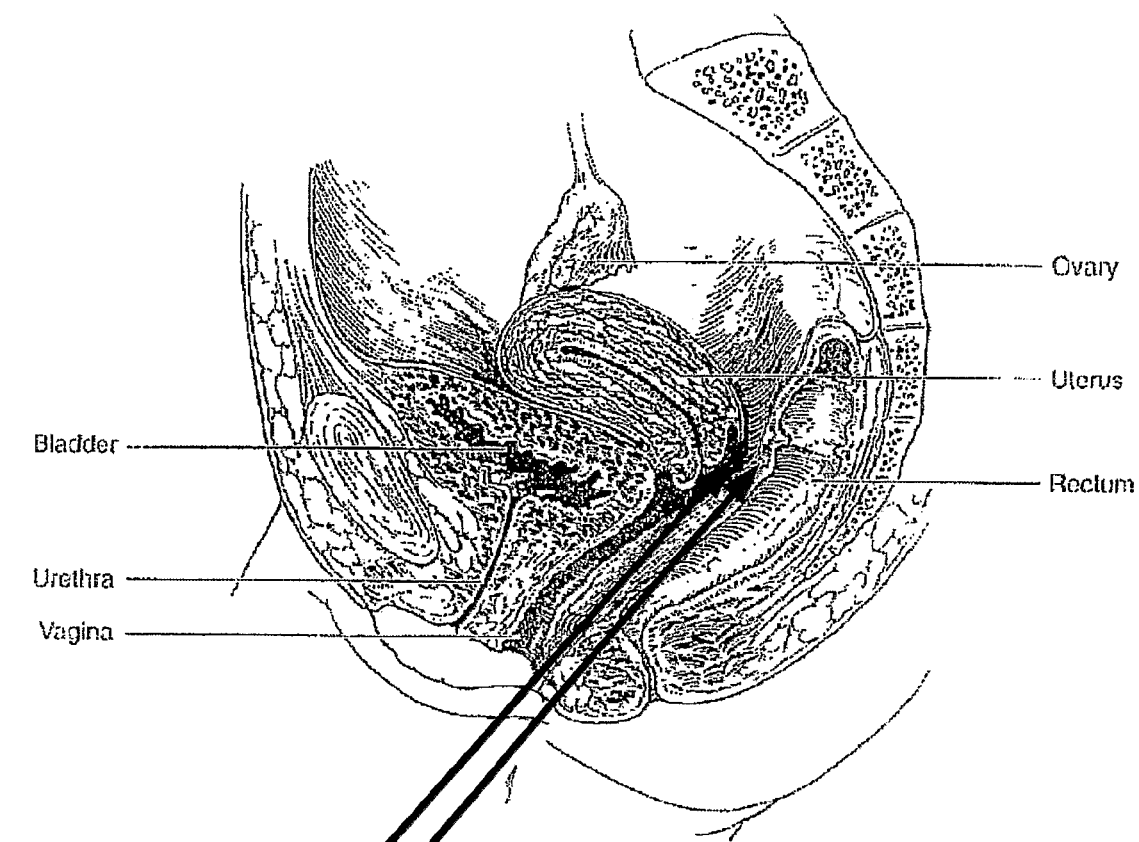
Fig. 6a
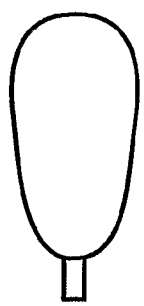  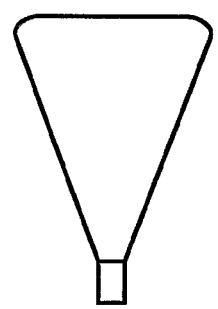 
Fig. 6b   Fig. 6c   Fig. 6d   Fig. 6e

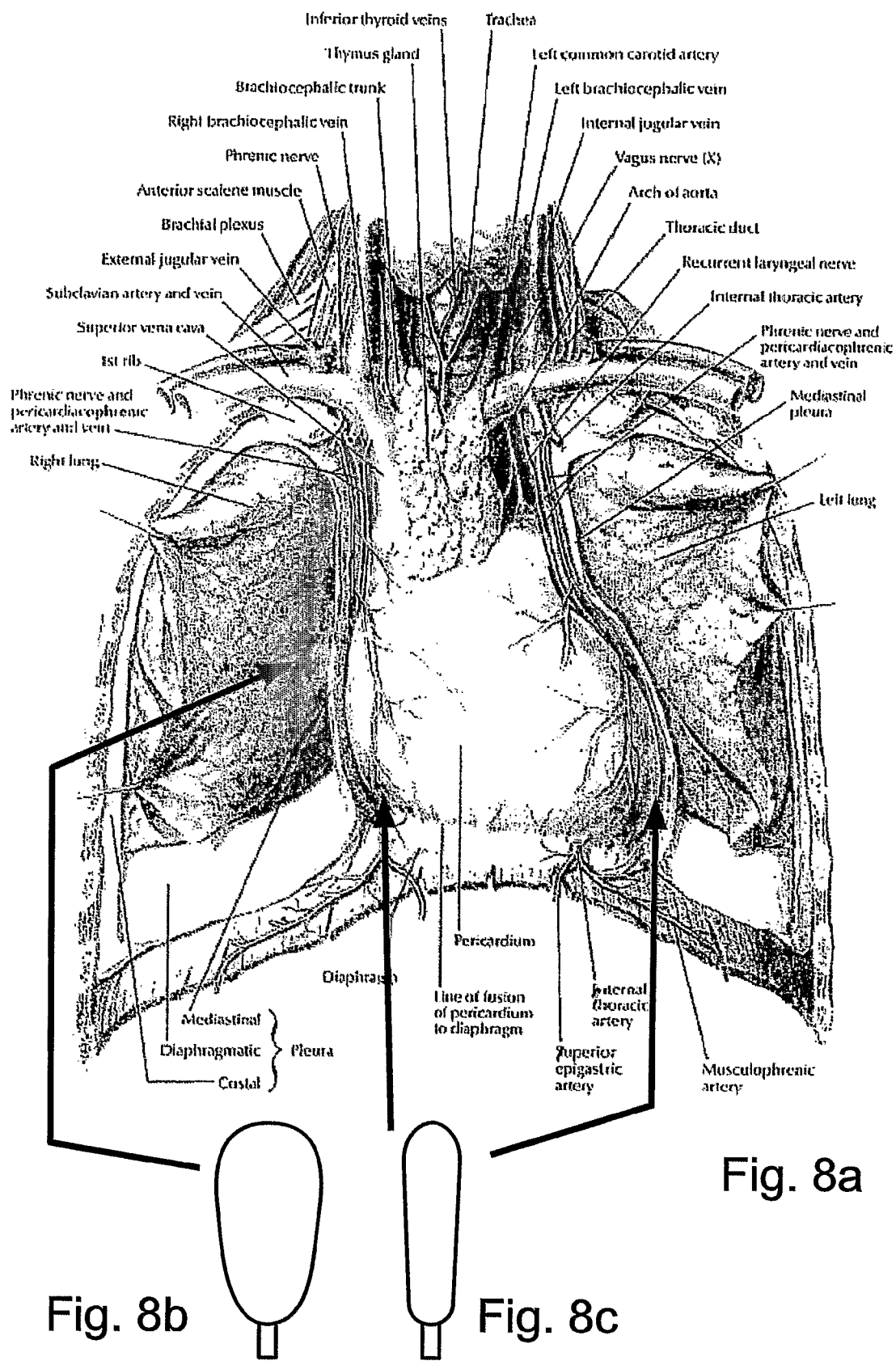

DEVICE SYSTEM AND METHOD FOR TISSUE DISPLACEMENT OR SEPARATION

RELATED APPLICATIONS

This application is a National Phase Application of PCT Application No. PCT/IL2005/000672 having International Filing Date of Jun. 23, 2005, which claims priority from U.S. Provisional Patent Application No. 60/581,769, filed on Jun. 23, 2004. The contents of the above Applications are all incorporated herein by reference.

FIELD AND BACKGROUND OF THE INVENTION

The present invention relates to a device, system and method for tissue displacement/separation and, more particularly, to a tissue displacement/separation device which can be used to protect healthy tissue from effects of treatment on adjacent treated tissues and yet minimize the physiological impact of displacement on the healthy tissue.

Removal or treatment of pathological tissue such as cancer or any malignant or benign growth or tumor caused by abnormal and uncontrolled cell division can be effected in any one of several well known approaches.

The most common form of treatment is surgery, followed by radiation (external or internal), chemical and thermal therapies. Examples of radiation therapies include but are not limited to external radiation beam therapy and interstitial brachytherapy, a technique in which radioactive sources are placed into the prostate gland, delivering radiation from within the prostate.

Thermal treatment approaches include but are not limited to cryotherapy and thermal ablation. In thermal ablation, a balloon or catheter filled with hot water is used to ablate target tissues. Cryosurgery, on the otherhand utilizes liquid nitrogen or argon gas expansion to injure tissue and is most often used when a tumor is small and cannot be removed using surgery.

Chemical ablation therapy includes use of a variety of chemical agents that kill cells exposed thereto. Chemical ablation utilizes chemical agents such as ethanol or hyperosmolar saline which are capable of causing necrosis to tissue exposed thereto.

Examples of other therapies that can be used for treatment include radio frequency ablation (RFA), a technique that employs high-energy radio frequency energy to destroy inoperable tumors and High Intensity Focused Ultrasound (HIFU), or Focused Ultrasound (FUS) which can be used to rapidly kill tissue such as tumors and to stop internal bleeding by cauterizing injured organs or blood vessels.

The above described treatments approaches can be practiced individually or in combination as adjuvant therapy. In any case, each of the above therapeutic approaches carries some degree of risk of injury to healthy tissues.

For example, during surgery, use of surgical instruments in small, tight spaces can lead to inadvertent tissue injury. Radiation therapy or localized release of chemical substances results in an intensity gradient between the treated tissue and healthy tissue and radiation or chemical injury to healthy tissues. As a result, the total energy or chemical dose for local treatment that can be applied to a tissue is limited by the dose that is inevitably transmitted to healthy adjacent tissues. Moreover, some tissues and organs are more sensitive to radiation and chemical damage than others and thus treatment of tissue adjacent to such tissues and organs can be severely limited.

Thus, there is a great need for an efficient, easy way to shield healthy tissues from the harmful effects of treatment on adjacent pathological tissues, while applying a relatively high and more efficient dose to the pathological tissue. Presently there are a few approaches suitable for separating healthy tissue from pathological/diseased tissue during treatment:

For example, U.S. Pat. No. 5,641,505 describes a material which can be used for tissue separation. The material comprises a porous flexible sheet or tube of a protein-free bioresorbable polymer having pores, which permits the passage of water and salts through the sheet or tube while restricting the passage of cells and other tissue particles. This device is limited in that use thereof in radiation or chemical therapy will lead to undesirable exposure of healthy tissue to radiation energy and chemical agents.

U.S. Pat. No. 5,733,316 discloses a method of providing thermal therapy to prostate tissue of a patient which includes inserting a mechanical separator or infusing a fluid, to separate human tissue to be treated, from non-target tissue, thereby providing thermal insulation and other beneficial effects, and applying the thermal therapy to the target tissue. The method is applied by locating the fluid infusing device at a location adjacent a portion of the patient's prostate and the patient's rectum to provide passage of a volume of a fluid from the device to target location without a containment structure. This approach is limited in that it cannot be used to displace tissue rather just infuse it with a liquid.

U.S. Pat. Application publication No. 20020147386 discloses a method and a device for stabilizing and retracting tissue during surgery, in particular internal tissue. Patches of material, preferably biodegradable, are adhered to tissue surfaces, by manipulation of the patches, for example directly with forceps, or via sutures attached to the patches, tissues can be retracted or otherwise manipulated with minimal trauma to the tissues. While this approach might be useful in some cases, it does not enable rapid uniform tissue displacement.

U.S. Pat. Application publication No. 20040094162 discloses the use of a filler to space a first tissue from a second tissue. Although this application described expandable devices such as balloons and sponges, it does not describe devices which can apply uniform pressure on the displaced tissue.

Thus, although prior art tissue separation approaches are capable of physically separating healthy tissue from treated tissue, and as a result at least partially shielding healthy tissue from the harmful effects of treatment, prior art approaches suffer from several inherent limitations the most prominent of which being an inability to uniformly displace tissue or retain a stable shape throughout the medical procedure.

There is thus a widely recognized need for, and it would be highly advantageous to have, a tissue displacement/separation device which can be utilized to protect healthy tissue from the harmful effect of treatment conducted on an adjacent pathological tissue while minimizing any harmful effects on healthy tissue that may be generated by displacement thereof.

SUMMARY OF THE INVENTION

According to one aspect of the present invention there is provided a tissue displacement/separation device comprising a bladder being expandable between a first tissue and a second tissue of a body, the bladder having an expanded shape being selected capable of displacing or separating the first tissue from the second tissue in a manner suitable for protecting the first tissue from an effect of a treatment applied to the second tissue.

According to yet another aspect of the present invention there is provided a tissue displacement system comprising: (a) a bladder being expandable between a first tissue and a second tissue of a body, the bladder having an expanded shape being selected capable of displacing the first tissue from the second tissue in a manner suitable for protecting the first tissue from an effect of a treatment applied to the second tissue; and (b) a guide being detachably attached to the bladder and being for introducing the bladder into a tissue.

According to further features in preferred embodiments of the invention described below, the bladder is designed capable of fluid expansion.

According to still further features in the described preferred embodiments the expanded shape of the bladder is selected from the group consisting of a pear shape, a fusiform shape, a discoid shape, a flattened shape, a triangular shape, a flattened cylindrical shape and any shape capable of displacing target tissue while minimizing injury thereto.

According to still further features in the described preferred embodiments the expanded shape of the bladder is selected capable of uniformly displacing or separating the first tissue from the second tissue.

According to still further features in the described preferred embodiments the expanded shape is further selected so as to minimize pressure and/or contact damages imposable by the bladder to the first tissue and/or the second tissue.

According to still further features in the described preferred embodiments the bladder is designed expandable via fluid filling.

According to still further features in the described preferred embodiments the bladder is designed expandable via an element capable of assuming a coiled rigid state.

According to still further features in the described preferred embodiments the bladder is composed of biodegradable material.

According to still further features in the described preferred embodiments the bladder comprises a thermal insulating/reflecting material.

According to still further features in the described preferred embodiments the bladder comprises radiation shielding material.

According to still further features in the described preferred embodiments the bladder comprises a transilluminative substance.

According to another aspect of the present invention there is provided A method of protecting a first tissue from an effect of a treatment applied to a second tissue comprising: (a) positioning an expandable bladder between the first tissue and the second tissue; and (b) expanding the bladder to an expanded shape thereby displacing or separating the first tissue from the second tissue and as a result protecting the first tissue from the effect of the treatment applied to the second tissue.

According to still further features in the described preferred embodiments the treatment is selected from the group consisting of thermal treatment, radiation treatment and drug treatment.

According to still further features in the described preferred embodiments the first tissue is selected from the group consisting of prostate, urinary bladder, rectum, vaginal wall, uterine cervix, uterus, kidney, liver, lung, mediastinum, mammary gland and the like.

According to still further features in the described preferred embodiments the positioning is effected via a guide.

According to still further features in the described preferred embodiments the expanding is effected by filling the bladder with a fluid.

According to another aspect of the present invention there is provided A method of forming a seamless bladder comprising: (a) providing a bladder template produced from material soluble in a first liquid; (b) coating the template with a solution of a polymer insoluble in the first liquid to thereby generate a polymeric coat on the template; and (c) exposing the template and polymeric film to the first liquid thereby dissolving the template and releasing the polymeric film and forming the seamless bladder.

According to still further features in the described preferred embodiments the first liquid is a hydrophilic liquid.

According to still further features in the described preferred embodiments the material soluble in a first liquid is gelatin or agar.

According to still further features in the described preferred embodiments the polymer can be a biodegradable polyester made from hydroxyl alkanoic acids, polyorthoesters, polyphosphazenes, polyphosphate esters, polyanhydrides and copolymers and blends thereof. Of particular interest are homo and copolyesters made from lactic acid, glycolic acid and caprolactone. The preferred polymers are those that are in clinical use that have already shown to be safe with predictable biodegradability, i.e. polylactide, poly(lactide-glycolide), poly(lactide-caprolactone) and polycaprolactone.

The present invention successfully addresses the shortcomings of the presently known configurations by providing a device system and method which can be easily used in separating/displacing and thus protecting healthy tissues from the harmful effects of treatment applied to adjacent pathological tissue.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3a-c illustrate prostate-rectal tissue (FIG. 3a) and an embodiment of the device of the present invention (FIG. 3b—front view; FIG. 3c—side view) particularly suitable for use in a treatment procedure applied within this tissue region (noted by arrow).

FIG. 4c—side view) particularly suitable for use in a treatment procedure applied within this tissue region (noted by arrows).

FIG. 5c—side view) particularly suitable for use in a treatment procedure applied within this tissue region (noted by arrow).

FIGS. 6a-e illustrate uterine tissue (FIG. 6a) and an embodiment of the device of the present invention (FIGS. 6b, d—front view; FIGS. 6c, e—side view) particularly suitable for use in a treatment procedure applied within this tissue region (noted by arrows).

FIG. 7c—side view) particularly suitable for use in a treatment procedure applied within this tissue region (noted by arrow).

FIGS. 8a-c illustrate thoracic tissue (FIG. 8a) and an embodiment of the device of the present invention (FIG. 8b—front view; FIG. 8c—side view) particularly suitable for use in a treatment procedure applied within this tissue region (noted by arrows).

FIG. 9c—side view) particularly suitable for use in a treatment procedure applied within this tissue region (noted by arrows).

DESCRIPTION OF THE PREFERRED EMBODIMENTS

Figure 1A:
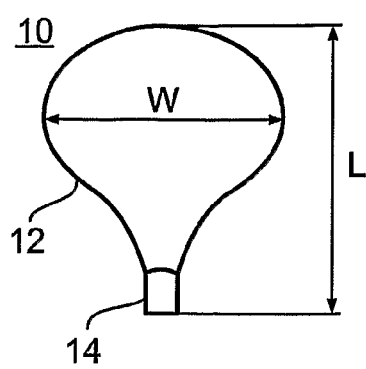
FIG. 1a illustrates one embodiment of the tissue displacement/separation device of the present invention.

The present invention is of a device system and method which can be used to protect a first tissue from the effect of treatment conducted on a second and adjacent tissue.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Treatment of body tissue via local release of chemical substances or provision of a radiation dose results in chemical/radiation gradient between the treated tissue and normal tissue. Therefore, the total radiation or chemical dose which can be applied to a tissue is limited by the dose that is inevitably transmitted to normal adjacent tissues.

To traverse this treatment limitation, several devices have been adapted for tissue protection during localized treatment of body tissues (see, the background section for examples). Although the above described prior art devices can be used to protect a tissue region from the harmful effects of a treatment conducted on an adjacent tissue, such devices either lack the shape necessary for effective tissue protection or are not effective in reducing the physiological impact on the tissue displaced.

Thus, according to one aspect of the present invention there is provided a tissue displacement/separation device which can be utilized to protect a body tissue from the harmful effects of treatment, such as thermal or radiation treatment.

As used herein the term "displacement/separation" refers to either moving one tissue away from another or by filling a void between tissues with a physical barrier.

The device of the present invention includes a bladder which is expandable between a first tissue and a second tissue of a body of a subject (preferably human). As used herein, the terms "first tissue" and "second tissue" can denote two tissue types (for example, prostate-rectum, uterus-rectum, uterus-small bowels, urinary bladder-uterus, ovary-bowels uterus-urinary bladder, liver-gallbladder, lung-mediastinum, mediastinum-lung, mammary gland-thoracic wall, esophagus-spine, thyroid-blood vessels, thyroid-pharynx and larynx, small bowels and large bowels-retroperitoneum, kidney-liver, pancreas-stomach, pancreas-spine, stomach-liver, stomach-spine, etc) or different tissue regions of the same tissue type. It will be appreciated that in the latter case, the two tissue regions can be naturally adjacent and attached by fibro-conjunctive tissue (e.g., lobes of a lung) and can be separated by the introduction of an incision.

In any case, the device of the present invention is designed such that an expanded shape thereof is selected capable of displacing the first tissue from the second tissue. Such physical separation optionally combined with a barrier effect of the device protects the first tissue from an effect of a treatment applied to the second tissue.

As used herein, the term "treatment" when used in context of the first and second tissues denotes any treatment which can be harmful to the untreated tissue (e.g. first tissue). Examples of treatments include radiation treatment, such as, for example, external radiation therapy using gamma irradiation, high energy photon beam therapy, electron beam therapy, proton beam therapy, neutron beam therapy, heavy particle beam therapy, conformal 3d radiation therapy, intensity modulated radiation therapy (IMRT), interstitial brachytherapy or any combination thereof. Treatment can also include drug treatment (local) such as alcohol tissue ablation or hyperosmolar ablation using NaCl crystals or hyperosmolar solution or physical tissue manipulation (e.g. dissection).

Thus, the present invention provides a device which is useful in protecting tissue from the harmful effects of various types of treatments including, but not limited to, externally provided radiation therapy such as, ionizing radiation, or non-ionizing radiation (microwave therapy, radiofrequency therapy, high intensity focused ultrasound therapy, etc), or interstitial therapy such as, for example, interstitial brachytherapy, interstitial thermal ablation, contact thermal ablation by hot liquid, high intensity focused ultrasound, thermoregulated rods, interstitial laser therapy with or without photodynamic agents, cryotherapy, interstitial chemical ablation, localized chemotherapy, etc. Such a device is also useful in invasive treatments, such as, surgical extirpation, when blunt dissection and separation of tissue can be difficult and can result in inadvertent injury to adjacent organs.

It will be appreciated that any number of the present device can be utilized to fill complex spaces in order to displace one tissue from another. The devices might be interconnected in order to maintain a functional protective structure. Multi-device structures might be suitable for physical separation in the peritoneal cavity wherein some of the interconnected devices serve as anchors to the body wall preventing movement and migration of the structure.

Figure 1D:
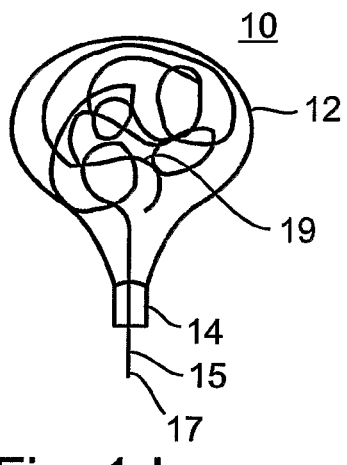
FIG. 1d illustrates an embodiment of the tissue displacement/separation device of the present invention in which the bladder is expanded using an elongated member capable of assuming a coiled state.
Figure 1B:
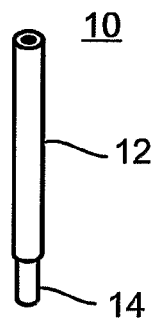
FIG. 1b is a side view of the device of FIG. 1, showing the bladder in a collapsed (rolled) state.
Figure 1C:
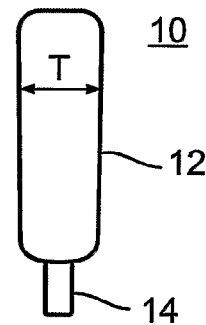
FIG. 1c is a side view of the device of FIG. 1, showing the bladder in an expanded state.

Referring now to the drawings, FIGS. 1a-c illustrates one embodiment of the device of the present invention which is referred to herein as device 10.

Device 10 includes a bladder 12 which can be constructed out of any biocompatible material. As used herein the term bladder refers to any chamber having an inner volume when expanded and substantially no inner volume when collapsed. Although FIGS. 1a-c illustrate a flat balloon shape having an expanded state length L (FIG. 1a e.g. from 1 to 20 cm), an expanded state width W (FIG. 1a e.g. from 1 to 20 cm) and an expanded state thickness T (FIG. 1c e.g. from 1 to 10 cm), it will be appreciated that bladder 10 can be fabricated in any shape suitable for uniform tissue displacement thus minimizing any localized pressure on the displaced tissue. Examples of bladder 12 shapes include, but are not limited to, a pear shape, a fusiform shape, a discoid shape, a flattened shape, a triangular shape and a flattened cylindrical shape.

Reducing or minimizing localized pressure on displaced tissue is important since it ensures that displaced tissue is supplied with ample blood flow and thus reducing the chances of localized ischemia. It will be appreciated that by selecting a shape that ensures such uniform pressure on the displaced tissue, the present device overcomes the deficiencies of prior art balloon-shaped displacement devices (e.g. U.S. Pat. No. 6,852,095) which can generate non-uniform pressure on displaced tissue (in particular soft tissues) and thus can lead to localized ischemia especially in long term procedures.

Examples of various bladder shapes which can be utilized by device 10 of the present invention are provided hereinbelow and in the Examples section which follows.

Device 10 can be constructed from any biocompatible material including, but are not limited to, polymers, such as, biodegradable polyesters made from hydroxyl alkanoic acids, polyorthoesters, polyphosphazenes, polyphosphate esters, polyanhydrides and copolymers and blends thereof. Of particular interest are homo and copolyesters made from lactic acid, glycolic acid and caprolactone. The preferred polymers are those that are in clinical use and have already shown to be safe with predictable biodegradability, i.e. polylactide, poly(lactide-glycolide), poly(lactide-caprolactone) and polycaprolactone. The selected polymers should fit the desired mechanical and physical stability of bladder 12 in vivo. A biodegradable polymer that retains its mechanical and physical properties when designed as a thin layer bladder, for at least 2 months is utilized to produce a bladder which needs to retain its mechanical and physical properties for two months in the body. In addition, the polymers should be film forming and flexible enough to enable folding of bladder 12 into a compact configuration that can be inserted within a tube that serves as dispenser for device 10 in vivo. The properties of the polymer compositions can be tailored to fit any requirements by either blending various polymers or mixing the polymer with hydrophobic or hydrophilic additives that alter the polymer properties. Such additives can be plasticizers that increase the flexibility of bladder 12, hydrophilic components such as poly(ethylene glycol) and minerals that increase hydrophilicity and serve as pore making agents. Hydrophobic components can be triglycerides, fatty acids and esters and other biodegradable polymers. The polymer structure and molecular weight play a significant role in designing the desired properties of the polymer composition.

FIG. 1b illustrates bladder 12 in a collapsed (e.g. rolled) state which is suitable for delivery using minimally invasive techniques (further described hereinbelow). FIG. 1c illustrates bladder 12 in an expanded state which is capable of effecting tissue displacement or separation.

One suitable approach for fabricating device 10 from biodegradable polymer solutions is provided in Example 1 of the Examples section hereinbelow. In the approach described, bladder 12 is constructed as a seamless structure by dipping a water soluble expanded bladder template in an organic polymeric solution and removing the formed polymeric bladder from the template by dissolving the template in water.

Device 10 can include a bioadhesive coating or any other physical mechanism which can decrease its mobility within the insertion site. This feature is important to minimize movement of device 10 from the site of application and thus guarantee optimal protection for the non-treated tissue.

Suitable bioadhesives include as carboxymethyl cellulose (CMC) and similar bioadhesive that are allowed for use in humans. CMC may be applied as dry film onto bladder 12. Following insertion and absorption of water such a film develops adhesive properties towards tissue. Bladder 12 can be configured with various surface structures such as pimples, grooves, bumps, microhooks, ridges or any combination thereof such that when expanded a friction between bladder 12 surface and displaced tissue is increased without affecting the functionality of the device.

Expansion of bladder 12 is conducted in-tissue following insertion and positioning of device 10. Such insertion and positioning can be effected by using a guide (a suitable guide is further described hereinbelow with respect to FIG. 1d). Following expansion such a guide can be kept attached to device 10 during short term procedures in which treatment is provided over a course of hours (e.g. thermal ablation) or it can be detached therefrom during longer procedures in which treatment is provided over a course of days, weeks or even months (e.g. long term radiation or interstitial procedures).

In the latter case, device 10 is preferably constructed from a biodegradable material such that device 10 degrades and is absorbed by the body over a predetermined time period or following absorption of a predetermined dose amount of treatment (e.g., radiation). To enable biodegradation, device 10 is constructed from polymers which are biocompatible and bioabsorbable, and yet posses mechanical properties suitable for maintaining the desired in-tissue shape. Such polymers can be prepared by synthetic or natural methods as long as the polymer is provided in a sufficiently pure form suitable for use in body tissues.

The polymers may be prepared from any combination of monomeric units or from natural semi-synthetic and synthetic biodegradable polymers and compositions. These units must, however, be capable of biodegrading in vivo to non-toxic components, which can be excreted or further metabolized.

The combination of units in the polymer must also be biocompatible, and not elicit an undesirable biological response upon implantation of device 10. The polymer may be biodegraded in vivo via hydrolysis, enzymatic cleavage, cell-mediated degradation, or by any other biologically mediated process. Since the need for tissue displacement may vary depending on the type and duration of treatment, it is desirable to have polymers with a range of degradation rates as well as a range of different properties. Generally, however, preferred polymers will degrade in a matter of weeks to months, preferably less than one year. Examples of suitable biodegradable polymers which can be used to fabricate device 10 include, but are not limited to, biodegradable polyesters such as, polylactide, poly(lactide-glycolide), poly(lactide-caprolactone) and polycaprolactone.

Preferably, the polymer is a polyester constructed from a hydroxy acid monomers. The hydroxy acid may optionally contain other functional groups and be substituted at any position, including heteroatoms between the hydroxy and acid groups. These hydroxy acids may be polymerized using synthetic methods or preferably using biological methods. In the latter case, the hydroxy acids may be derived in vivo from a non-hydroxy acid source. Suitable methods for preparing polyesters are described in Williams, S. F. and Peoples, O. P. CHEMTECH, 26:38-44 (1996), Hocking, P. J. and Marchessault, R. H. "Biopolyesters", G. J. L. Griffin, Ed., "Chemistry and Technology of Bioabsorbable Polymers," Chapman and Hall, London, 1994, pp. 48-96.

The polyester can include one or more non-ester linkages in the main polymer chain which can be configured susceptible to cleavage in vivo. Suitable non-ester linkages may include amides, urethanes, carbonates, iminocarbonates, oxalates, oxamates, orthoesters, anhydrides, phosphazenes, glycosides, and ethers. Incorporation of such linkages can be used to alter biodegradation rates, tailor mechanical, surface, or other properties of the polymer, improve processing and handling of the materials, and/or to provide methods for attachment of other compounds to the polymers (e.g., contrasting or treatment agents described below).

A typical polymer suitable for fabricating bladder 12 can include: D,L-polylactide, lactide-glycolide copolymers, PEG-PLA copolymers, and polyesters and polyamides and other biodegradable compositions that form a strong film that can maintain an expanded state for extended time periods.

The time required for a polymer to degrade can be defined by selecting appropriate monomers. Differences in crystalline structure also alter degradation rates. Actual mass loss initiates when the polymer matrix degrades to oligomeric fragments that are small enough to be water soluble. Hence, initial polymer molecular weight influences the degradation rate. Degradable polymers containing water-soluble polymer elements have been previously described, see, for example, Sawhney et al., (1990) "Rapidly degraded terpolymers of dl-lactide, glycolide, and ε-caprolactone with increased hydrophilicity by copolymerization with polyethers," J. Biomed. Mater. Res. 24:1397-1411. Degradation rate and thus polymer selection is determined according to the use of device 10. For example, during cryotherapy and thermal ablation a polymer with a degradation time period of a few hours to one or two weeks is selected, during external beam radiation a polymer with a degradation time period of 5 to 6 weeks is selected, while during brachytherapy a polymer with a degradation time period of a few months is selected.

It will be appreciated that permanent implantation (preferably of a degradable device) is particularly useful in that it enables multiple treatment sessions without having to repeatedly insert and position a tissue protecting device. A device designed capable of such permanent implantation is particularly useful in cases where a treated individual is subjected to several treatment sessions (e.g., radiation) over an extended time period (e.g. weeks). In such a case, repeated implantation of a tissue protective device and thus repeated discomfort to the individual can be avoided by using device 10 of the present invention.

As is mentioned hereinabove, device 10 displaces or separates one tissue from another when bladder 12 is expanded.

Bladder 10 can be expanded using one of several approaches. To enable expansion, device 10 preferably includes a port 14 through which bladder 12 can be expanded or collapsed. Port 14 is preferably a small diameter port with a diameter which is $\frac{1}{5}$ to $\frac{1}{100}$, preferably $\frac{1}{5}$ to $\frac{1}{20}$ of the expanded thickness or width of expanded bladder 12. Port 14 can be a fluid filling port, in which case bladder 12 can be expanded by using a gas or a liquid and collapsed via emptying. Alternatively, port 14 can be utilized to introduce a solid yet elastic element that can fill bladder 12 such that it assumes a semi rigid expanded state. As is shown in FIG. 1d, such a solid element can be, for example, an elongated member 15 (e.g. a wire or thread 3-5 mm in diameter) that can be forced into a linear state 17 and thus can be introduced into bladder 12 through port 14, but when released naturally assumes a coiled structure 19 that forces bladder 12 to assume an expanded state. Such a wire can have a circular, elliptic, triangular rectangular or stellate profile and can be solid or hollow. The profile can be uniform along the entire length of the wire or it can change intermittently in order to permit easier folding inside bladder 12. Bladder 12 can also be filled with beads that can optionally be interconnected by a thread or wire. It will be appreciated that such wire or bead expansion traverses the need for bladder sealing. Elongated member 15 can be made from a biocompatible and optionally biodegradable elastic material such as, for example, polylactide, poly(lactide-glycolide), poly(lactide-caprolactone) and polycaprolactone or a Shape Memory Polymer (SMP) made for example from multi block copolymers of lactide and caprolactone which can assume an elongated state when heated and a coiled state when cooled to body temperature.

Although any of the above approaches can be effectively utilized to expand/collapse bladder 12, liquid expansion is presently preferred for its added benefits and ease of use.

Use of a liquid provides several advantages. It enables bladder 12 to conform to the tissue displaced and thus apply uniform pressure thereupon. It enables introduction of useful agents, such as contrasting agents or treatment agents into bladder 12 and it can serve as an excellent physical barrier against heat, or radiation by introducing substances that absorb radiation such as iodinated agents or fluorocarbons.

Any liquid can be utilized to expand bladder 12, preferably the liquid utilized is biocompatible and physiological such as 0.9% saline, Ringer solution or Hartman solution. Use of a physiological liquid is particularly advantageous in that it provides a good sonographic window which is essential in procedures that necessitate ultrasound guidance for introduction of the balloon or for local therapy or follow up (e.g. trans rectal ultrasound for therapy of the prostate). Additionally, in case of side effects such as pain or discomfort or local infection the balloon can be easily collapsed using a thin needle.

In the liquid expansion configuration, bladder 12 is preferably constructed from a fluid impermeable material such that an expanded state thereof can be retained following filling. Examples of suitable liquids include, but are not limited to, water, saline and the like.

As is mentioned above, the liquid can include agents that can be useful in imaging, radiation and/or thermal treatment modalities.

For example, to enhance imaging, the liquid in bladder 12 can include imaging contrast agents such as iodinated or baritated substances or various fluorocarbons, which are useful in fluoroscopy or CT scanning; echogenic or anechoic substances which are useful in ultrasound imaging, MRI contrasts agents such as godolinium, radioactive isotopic substances for SPECT, or PET scanning. To protect tissue from radiation, agents such as iodinated substances, baritated substances, fluorocarbons, and the like can be included in the liquid. Agents active in tissue healing/repair can also be added to the liquid in which case, bladder 12 is preferably constructed so as to enable release of such agents to the tissue. It will be appreciated that the above described agents can alternatively be added or incorporated into the material of bladder 12 in which case, such agents can be released upon degradation of device 10, or following absorption of a dose of treatment (e.g., radiation).

Port 14 can be constructed with a plurality of channels so as to enable circulation of a liquid with expanded bladder 12. Such circulation of liquid enables tissue cooling or heating when necessary. For example, when thermal ablation is conducted, cooling of non-treated tissue can be effected via circulation of cold water. It will be appreciated that in such cases, bladder 12 is preferably constructed such that the cooled side (facing non-treated tissue) is more thermally conductive then the side of bladder 12 facing treated tissues.

Port 14 can include additional channels that enable introduction of a viewing device such as endoscope or an ultrasonic transducer, which can be to assess the effect of treatment, or to introduce therapeutic probes such as radiofrequency, or high intensity ultrasound probe or to introduce optical fibers which can be used for probing or for transillumination.

It will be appreciated that various gelling liquids can also be utilized to expand bladder 12. Such gelling liquids can be used to further enhance the tissue protective qualities of bladder 12 by providing a physical cushion capable of further protecting the displaced/separated tissue from physical trauma which can result from displacement or treatment. Gelling materials are also advantageous in that in case of rupture, the gel will be locally retained and will not dissipate. Examples of gelling liquids that can be utilized to expand device 10 of the present invention include, but are not limited to, absorbable haemostatic agents such as, gelatin, cellulose, bovine collagen and biodegradable synthetic adhesives such as, poly ethylene glycol (PEG).

The liquid utilized to expand bladder 12 can also include a fluorophore or any other trans-illuminative substance which can emit or reflect light which can be used to guide a procedure performed on the treated tissue. Alternatively such a light reflecting/emitting substance can be incorporated into the material of bladder 12.

As is mentioned hereinabove, device 10 of the present invention is preferably inserted and positioned within tissue using a guide.

Thus, according to another aspect of the present invention there is provided a system which can be utilized for tissue displacement or separation.

Such a system includes device 10 and a guide which is detachably attached to device 10. The guide serves to insert and position device 10 and to expand bladder 12 when in position.

The guide can be a thin catheter or a blunt tip needle (canula), of about 1-5 mm in diameter, preferably 2-3 mm in diameter. The guide posses a lumen through which a bladder-expanding fluid (or rigid element) can be conducted from a device such as a syringe (in the case of fluid) to bladder 12. Bladder expansion can be monitored by using different imaging technique such as: direct view, transillumination, fluoroscopy, endoscopic or laparoscopic US, US, CT scan, MRI, endoscopic view, etc. The guide is preferably constructed from biomedical grade elastomer such as PVC or polyurethane.

In cases where device 10 is left within the body, the guide is detached from the device 10 which preferably remains inflated by self sealing of port 14. Such self-sealing can be effected by a one way valve incorporated into port 14, by viscosity of a bladder expanding liquid (e.g. one that forms a gel) or by a biodegradable sealing mechanism such as that described below with respect to FIG. 1e. A cutting catheter made from bio-compatible material and having a sharp edge may be used to detach device 10 from the guide if necessary.

Figure 1E:
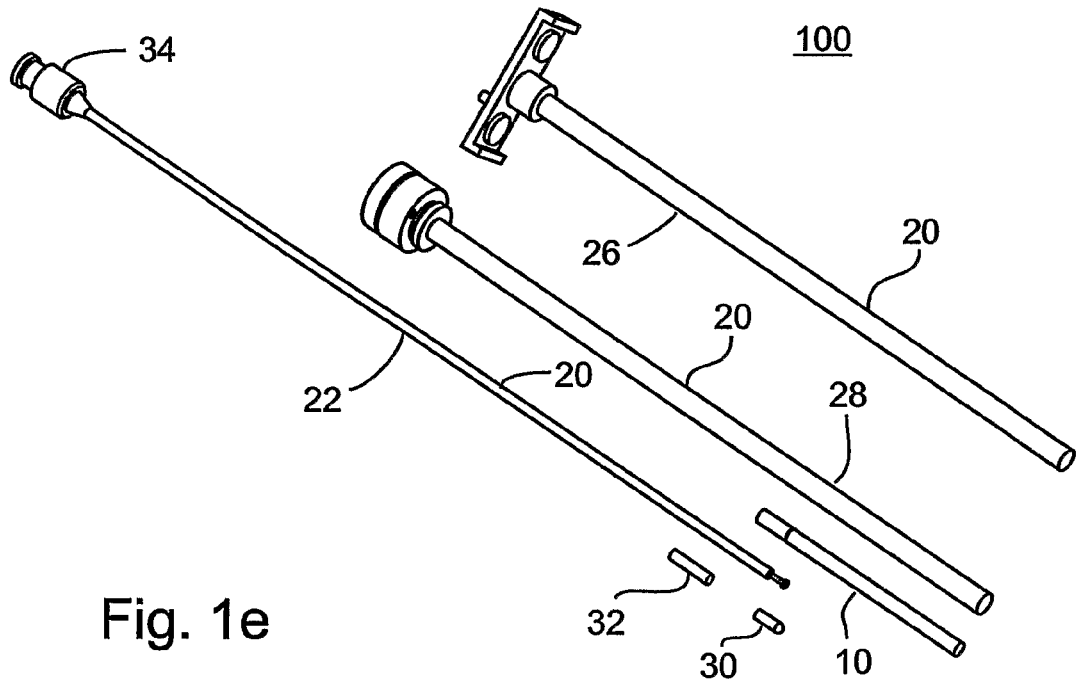
FIG. 1e illustrates the tissue displacement/separation system of the present invention.

FIG. 1e illustrates one embodiment of the system for tissue displacement or separation which is referred to herein as system 100. System 100 includes device 10 which is shown in a collapsed (rolled) state. System 100 also includes a guide 20 which includes a needle 22 for attaching to port 14 of device 10, a packaging sheath 28 for holding device 10 and a dilator sheath 26 for holding packaging sheath 28.

Needle 22 and dilator sheath 26 are used in a manner similar to the well known Seldinger technique (The Seldinger technique. Reprint from Acta Radiologica 1953; AJR Am J. Roentgenol. 1984 January; 142(1):5-7). This minimally invasive technique is used to provide a device or substance access to a specific location in the body through a dilator sheath. Thus, positioning of dilator sheath 26 within a body tissue enable delivery of device 10 (rolled or folded inside packaging sheath 28) to a specific body location. Once positioned, device 12 is deployed by retracting both sheaths and expanding bladder 12 (via for example syringe connected to port 34 of needle 22) at the proper location and orientation. Device 10 is then sealed to prevent deflation by using the one way valve or self sealing mechanism described above. Alternatively, port 14 of device 10 can be sealed by using a biodegradable plug 30 which is forcefully stuck into a non resilient biodegradable tube 32 attachable at port 14. Alternatively, sealing can be performed by external compression of port 14 with an elastic constricting ring or by knotting of port 14.

When used in long term procedures, needle 22 of guide 20 is detached from expanded and sealed device 10 and removed from the body, otherwise, following procedure, needle 22 with attached device 10 are removed from the body along with dilator sheath 26 and packaging sheath 28.

Examples 3-8 of the Examples section which follows describe use of system 100 in several treatment procedures.

Thus, the present invention provides a device and system which can be utilized in protecting tissue from the harmful effects of treatment. As is described herein, one of the notable features of the present device is its ability to uniformly displace/separate tissues in a manner which minimizes tissue damage, while being implantable and optionally biodegradable thus enabling repeated treatment to a tissue region without necessitating repeated in-tissue positioning procedures.

As used herein the term "about" refers to +10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds support in the following examples.

EXAMPLES

Reference is now made to the following examples, which together with the above descriptions, illustrate the invention in a non limiting fashion.

Example 1

Bladder Fabrication

An important feature of the bladder of the present device is its ability to retain a predetermined shape once expanded.

This feature is critical for optimal tissue displacement/separation and minimization of localized tissue pressure. For the same reason, the bladder of the present device is preferably fabricated with a smooth seamless external surface. To facilitate these requirements, a unique production process was formulated. The process combines two production concepts, a permutation of "lost wax" casting and dip molding.

Dip molding is used to "build" the bladder walls by dipping a pre-shaped model of the bladder in a solution made of a polymer dissolved in organic solvent. The pre-shaped model is made of materials that are later extracted from the internal volume of the bladder through its orifice. Unlike the well known "lost wax" casting method, wax cannot be used since it dissolves in organic solvents such as alcohols, chlorinated hydrocarbons, alkanones, acetonitrile, dialkyl ethers, cyclic ethers, acetate alkyl esters, and common aromatic solvents. Typical solvents include butanol, dichloromethane, chloroform, butanone, acetone, acetonitrile, disiopropyl ether, tetrahydrofurane, dioxane, ethyl and butyl acetate, and toluene. The only casting agents that can be used are hydrophilic in nature and include protein, polysaccharides and various synthetic and semisynthetic polymers. Examples include, but are not limited to, gelatin, agar, alginate, hydroxypropylcellulose, poly(acrylic acid-co-methylmethacrylate), chitosan, dextran, and arabinogalactane.

Alternatively, alloys with a low melting temperature (e.g., alloys including rare earth metals) can be used for the casts. These casts are heated and melted and extracted at a temperature lower than the melting temperature of the coating polymer.

The bladder shape is based on the anatomy of the target location and is designed to achieve an optimal separation with minimal local pressure on the surrounding tissues/organs.

The following provides a stepwise description of the bladder production process of the present invention.

Figure 2:
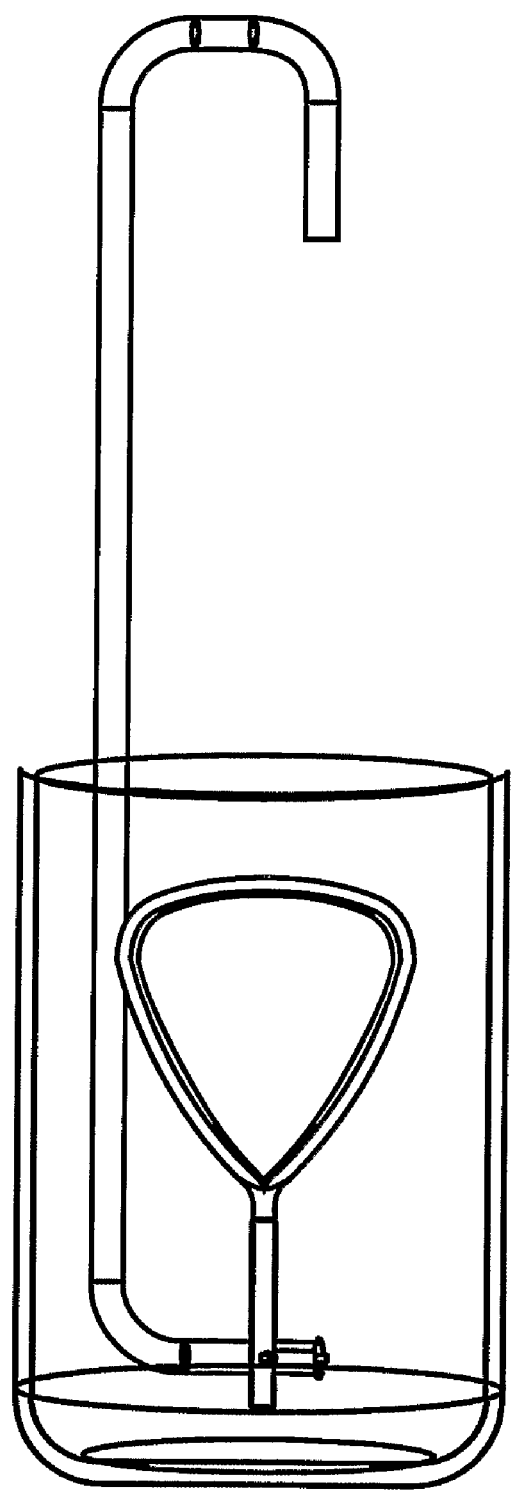
FIG. 2 illustrates the dipping method used to fabricate the seamless bladder utilized by the device of the present invention.

(i) Prepare mold of the required bladder shape.
(ii) Inject hot casting agent (10% W/V agar in water) and wait 15 minutes for the cast to cool down and harden.
(iii) Extract bladder model from mold and attach to dip molding handle (See FIG. 2).
(iv) Dip the model inside the dipping solution (e.g. 10% W/V biodegradable polymer dissolved in an organic solvent) at a constant speed (~20 cm/min.)
(v) Repeat step (iv) several (e.g. six) times until required coating thickness is acquired.
(vi) Wait until organic solvent evaporates (2-3 hours).
(vii) Extract casting agent through bladder orifice by heating the model and washing with water.

It will be appreciated that when the bladder is filled with a biodegradable fiber, it can be alternatively fabricated by welding or gluing together of two films of the bladder material. "Pressure forming", "film extrusion" or "blown film" methods are used to prepare the films. The films are then welded along the bladder external path using an accurate and controlled ultrasonic energy or glued using an accurate deposit of organic solvent along the gluing path.

Example 2

Prostate Cancer

Prostate cancer is the most common malignancy in men; 220,000 new cases are diagnosed each year in US and 50,000 patients undergo radical prostatectomy each year in the U.S. During the last few years there is an increasing trend to perform this surgery via minimally invasive techniques such as laparoscopic radical prostatectomy.

In radical prostatectomy (using either the open or the laparoscopic approach), the device of the present invention is inserted into the space between the rectum and prostate (see FIG. 3a) using the transperineal approach which is guided by trans-rectal ultrasound. Initially a thin 22 to 18 gauge needle is introduced into this space under trans-rectal ultrasound guidance and this virtual space is enlarged by injecting 5 to 20 cc of physiological liquid such as, for example, 0.9% sterile saline. A guide wire is inserted through the needle into this space; the needle is removed and a dilator is used to enlarge the tract; an introducer sheath is passed over the dilator and the dilator and the guide wire are removed; the folded device with its sheath measuring between 2 and 3 mm in diameter are introduced through the introducer sheath and the bladder component is deployed and expanded in the space between the rectum and prostate in the proper orientation. A pear shaped non distensible bladder 3 to 5 cm length, 3 to 5 cm width and 1 to 2 cm height (see FIGS. 3b-c) is preferably used. Upon expansion with either a biodegradable material or physiological solution, the bladder thickness will range between 10 to 20 mm. A specific bladder size corresponding to the size of the prostate in that particular patient will be used. Thereafter, an optic fiber can be introduced into the bladder through the needle and the needle can be removed. During the dissection of the prostate from the rectum the optical fiber is used for illumination and the inflated space between the rectum and prostate is viewed through the laparoscope by transillumination. Using such an approach, the borders of the prostate can be clearly seen and the prostate can be safely and rapidly dissected from the rectum and from the erectile nerves laying on the rectal side. In such a procedure, the device bladder is preferably filled with a gel, in which case puncturing of the bladder wall with a surgical instrument or damage thereto caused by thermal energy will not lead to loss of tissue displacement. Following the procedure, the bladder and the gel are removed using suction and laparoscopic instruments.

Approximately 100.000 patients undergo prostate radiotherapy in the U.S. each year. Half of these cases are performed via external beam radiation and the other half via brachytherapy. In prostate irradiation, the device of the present invention is preferably a pear shaped bladder 3 to 5 cm in length, 3 to 5 cm in width and 1-2 cm in thickness when expanded. The bladder is inserted into the correct space between the rectum and prostate as described above under local anesthesia. The bladder is then deployed and filled with physiological liquid or gel to its final dimensions and in the proper orientation. The catheter is then detached from the inflated bladder and the bladder is sealed in order to prevent deflation. Such sealing may be performed by using a biodegradable plug as described above or by tying of the biodegradable feeding tube. The bladder is sealed for the duration of the radiation therapy thus preventing its collapse. Patients undergo 30 to 40 sessions of radiation to the prostate 70 to 84 Gy on an ambulatory basis over a period of 5 to 6 weeks. Therefore, the bladder and/or the gel are chosen in such way so as to degrade following this period of time. Moreover, a radiation barrier in the form of a iodinated substance or fluorocarbons might be introduced into the bladder and/or the gel in order to further reduce exposure of the rectal wall, erectile nerves and bladder base to radiation and therefore permit use of a higher radiation dose (e.g. more than 80 Gy or 8000 rads). A radiotracer can optionally be used in order to enable delineation of the prostate during radiotherapy. The urinary bladder and external urinary sphincters can be additionally protected by using additional spacers on the anterior surface of the prostate at its base and between the sphincter and prostate apex. Moreover, since these spacers compress the prostate and separate adjacent tissues, the respiratory movements of the prostate are reduced permitting a more accurate dose delivery to the prostate.

The device of the present invention can also be used in prostate cancer cryotherapy. In such cases, a transperineally positioned device having thermal insulation and additional ports for hot water circulation or a device provided with thermal inducible means is utilized. In the latter case, the device can incorporate a thermal inducible gel or carbon particles that can be heated via a remote radiofrequency source situated in the rectal lumen for example, or by using a magnetic field.

A similar device can be used in thermal ablation treatment of prostate tumors or benign hyperplasia of the prostate. In such cases, intermittent or continuous liquid circulation might be used for cooling the rectal wall and erectile nerves. Additionally, when using a spacer bladder a heat reflective coating on the side facing the prostate might be used to reflect the radiation energy away from the rectum and back towards the prostate.

Example 3

Cholelithasis

Tissue displacement can also be performed during laparoscopic cholecystectomy. Approximately 400.000 such cases are performed each year in U.S. mostly for cholelithasis.

Figure 4A:
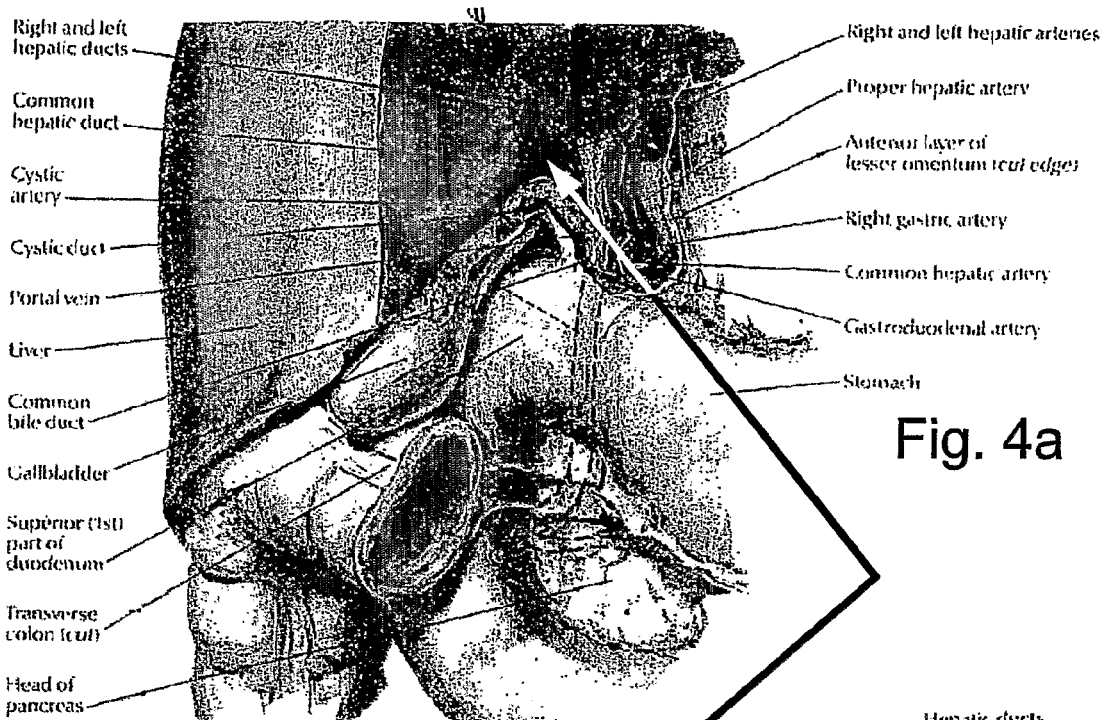
FIGS. 4a-c illustrate liver/gallbladder tissue (FIG. 4a) and an embodiment of the device of the present invention (FIG. 4b—front view.
Figures 4B, 4C:
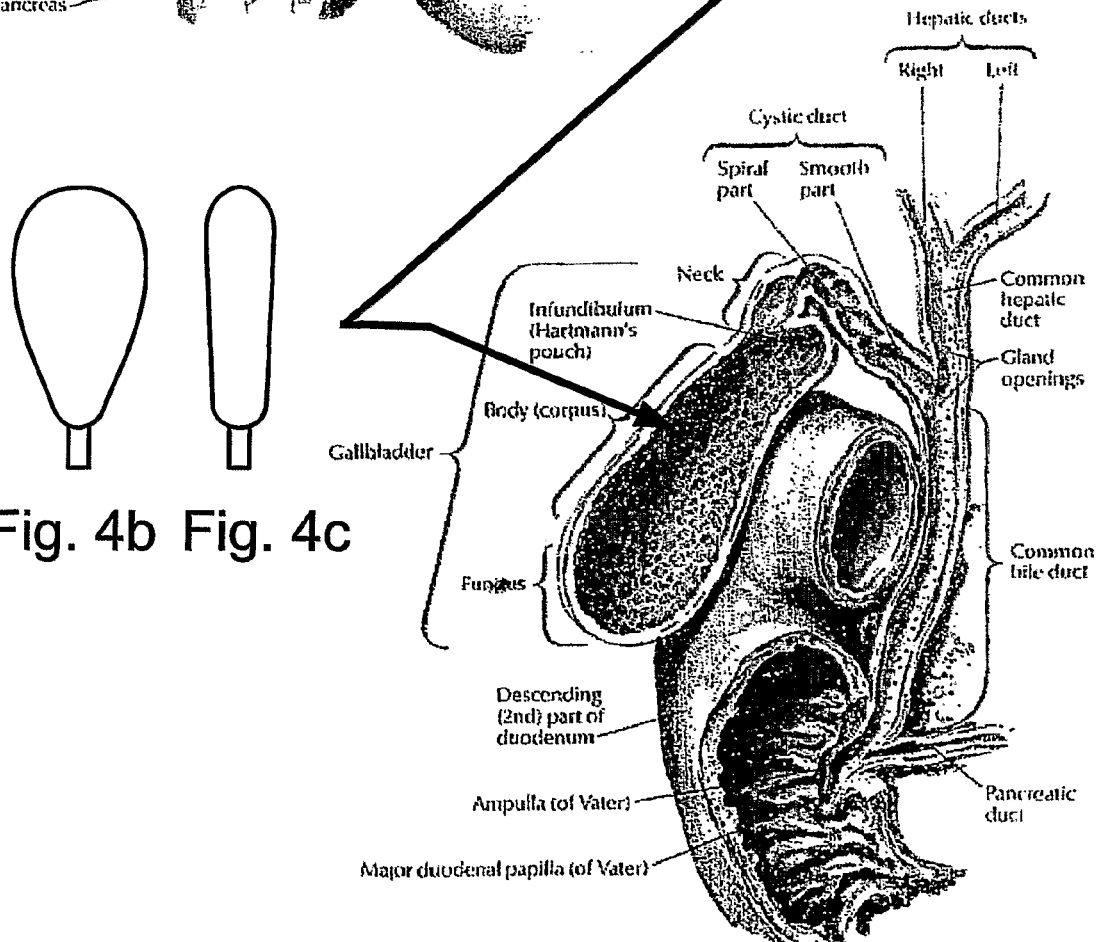

In cholecystectomy the bladder is preferably an elongated (5 to 7 cm long, 3 to 5 cm wide and 1 to 2 cm thick) shape (See FIGS. 4b-c). The device is preferably introduced between the gallbladder and liver in order to separate these organs and facilitate dissection (see FIG. 4a).

The bladder is folded in an encasing sheath and connected to a feeding catheter and the device is introduced through a 5 mm port within the peritoneal cavity. Initially minimal hydro-dissection is performed between these organs to create a space, then the device folded within the encasing sheath is introduced into this space, the sheath is removed and the bladder is expanded with a liquid or a gel. The catheter is then detached from the expanded bladder and the bladder is sealed in order to prevent deflation. Catheter detachment enables introduction of surgical instruments through the catheter port and dissection of the gallbladder from the liver. Use of a haemostatic agent such as fibrin, thrombin, alginate, gelatin or cyanacrylate (optionally incorporated into the bladder) enables homeostasis of the bleeding regions.

Example 4

Large Bowel Tumors

Tissue displacement can also be performed during laparoscopic colectomy. Approximately 300.000 such cases are performed each year in USA mostly for large bowel tumors.

Figures 5B, 5C:
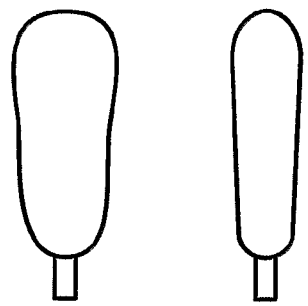
FIGS. 5a-c illustrate colorectal tissue (FIG. 5a) and an embodiment of the device of the present invention (FIG. 5b—front view.
Figure 5A:
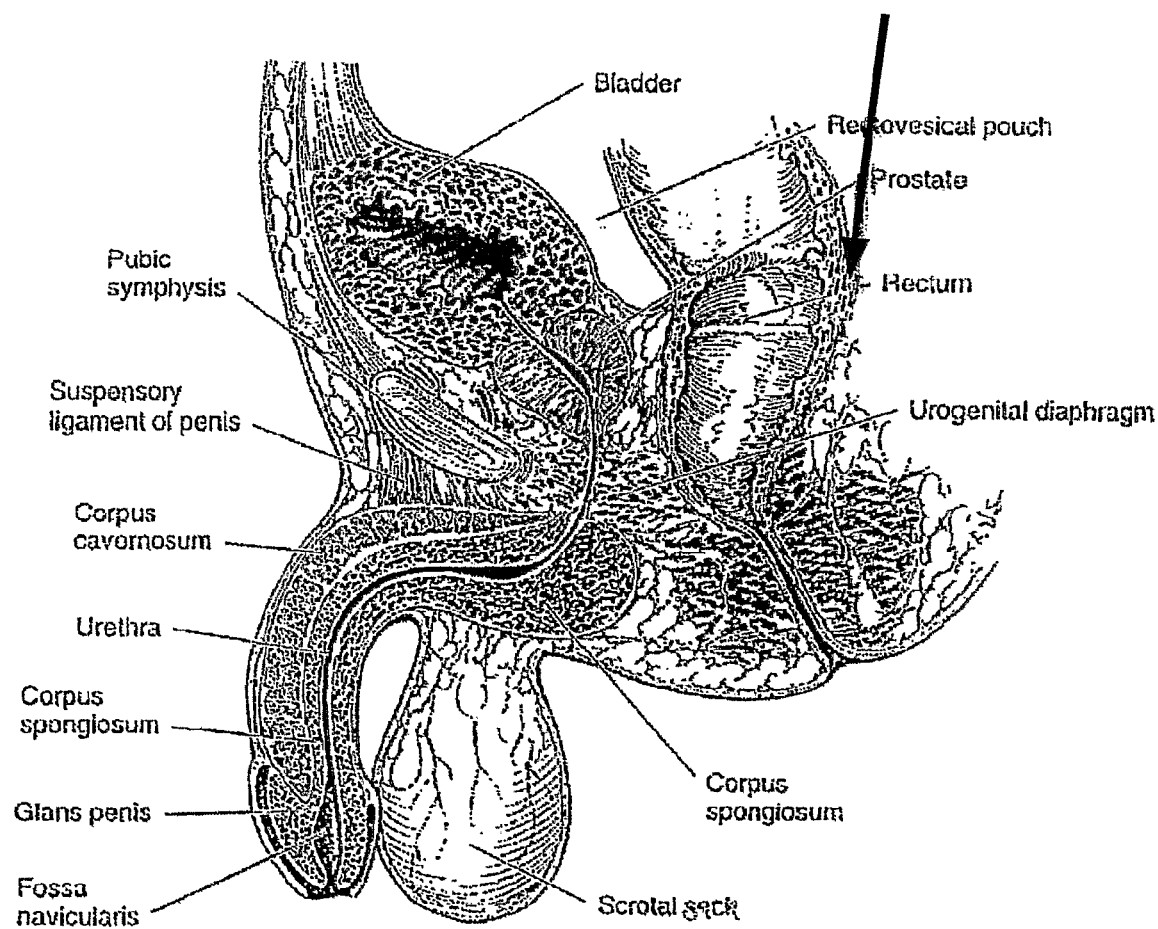

In colectomy an elongated bladder 10 to 20 cm long, 3 to 7 cm wide and 1-3 cm thick (when expanded) is preferably used (see FIGS. 5b-c). The bladder in its encasing sheath is introduced between the right colon and retroperitoneum or between the left colon and retroperitoneum or between the rectum and sacrum or rectum and urinary bladder in order to separate these tissues and facilitate dissection (see FIG. 5a). Initially minimal hydro-dissection is performed between these organs to create a space, then the device in its encasing sheath is introduced within this space, the sheath is removed and the bladder is expanded using a liquid or a gel in the proper orientation.

The catheter is then detached from the expanded bladder and the bladder is sealed in order to prevent collapse. Catheter detachment enables introduction of surgical instruments through the catheter port and dissection of tumor tissue.

Example 5

Cancer of the Uterine Cervix

Cancer of the uterine cervix is one of the most common tumors in women, accounting for more then 100,000 of cases annually in the U.S. Most of these cases are treated by cavitary radiation therapy. During this therapy, radiation may injure the rectum, bladder and small bowels.

The device of the present invention is inserted between the rectum and posterior vaginal wall/uterine cervix through posterior vaginal wall or through the perineum (see FIG. 6a) under trans rectal or trans vaginal ultrasound guidance. An extension of the bladder into the Douglas pouch or an additional device may be provided to push up the bowels. The folded device and sheath measuring between 2 and 3 mm in diameter are introduced through the introducer sheath and the bladder is deployed and expanded in the proper orientation in a space created (as described above) between the rectum and vagina/uterine cervix. An elongated bladder 3 to 10 cm in length, 3 to 5 cm in width and having a variable (expanded) thickness of 1 cm in the inter-rectal vaginal space to 5 cm in the distal Douglas pouch position (see FIGS. 6b-e).

The catheter is then detached and the bladder sealed as described above. Radiation therapy is then administered. Patients with Stage IB to IVB squamous cell carcinoma of the cervix (staging determined according to the International Federation of Gynecology and Obstetrics) are treated with a combination of external beam radiotherapy (EBRT) and high-dose rate intracavitary brachytherapy (HDR-ICBT). For patients with early-stage disease, 20 gray (Gy) of EBRT are delivered to the whole pelvis, followed by 24 Gy (in 4 fractions) of HDR-ICBT and 30 Gy of central-shielding EBRT. For patients with advanced-stage disease, 20-40 Gy of whole pelvic EBRT are administered, followed by 24 Gy (in 4 fractions) of ICBT and 30-10 Gy of central-shielding EBRT. The overall treatment time is approximately 6 weeks.

Example 6

Rectal Cancer

Rectal cancer is a common tumor accounting for 145,000 new cases each year in the U.S. alone. Thirty to forty percent of cases undergo preoperative or postoperative external beam irradiation. This treatment may cause injury to the urinary bladder, vagina and small bowels.

Figure 7A:
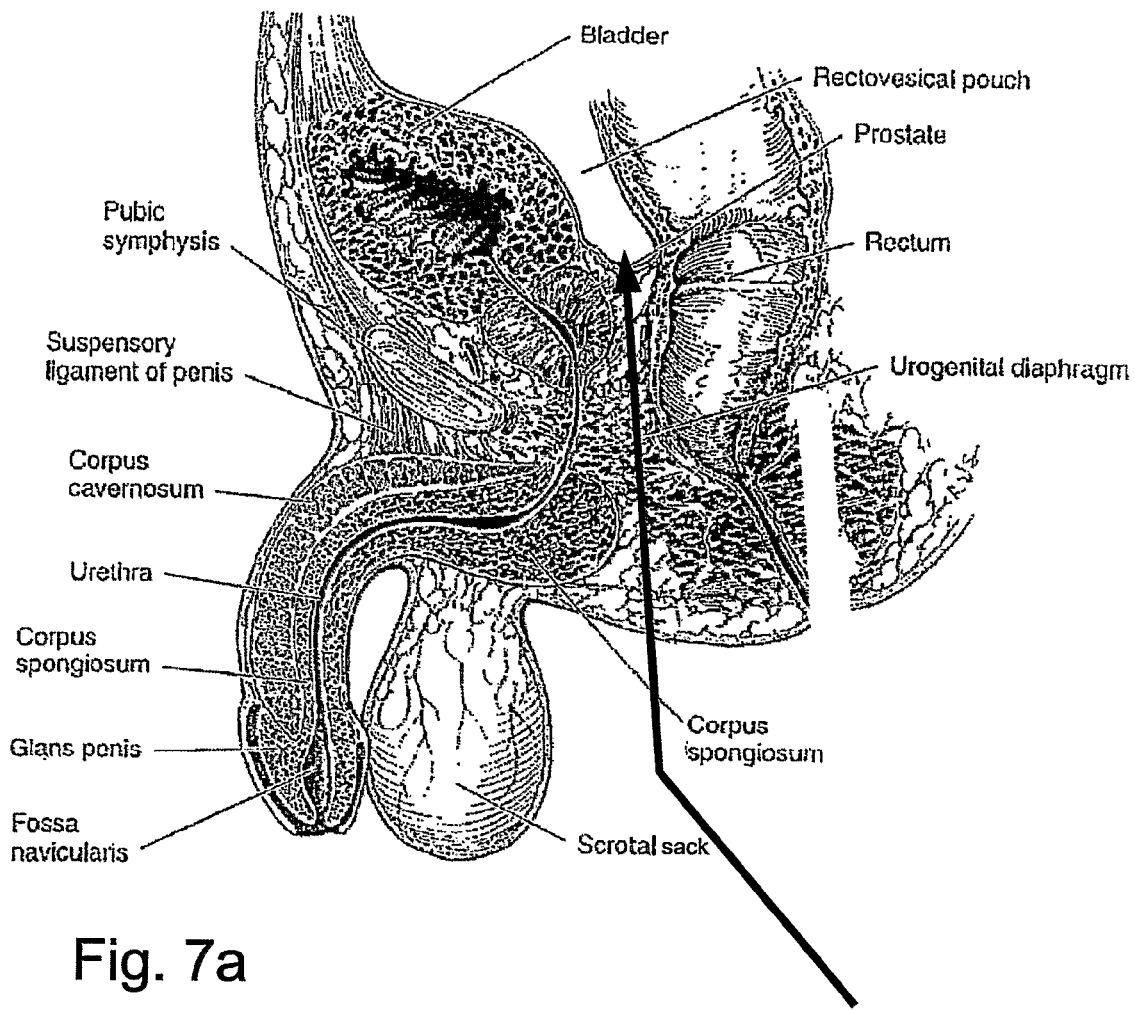
FIGS. 7a-c illustrate rectal tissue (FIG. 7a) and an embodiment of the device of the present invention (FIG. 7b—front view.
Figures 7B, 7C:
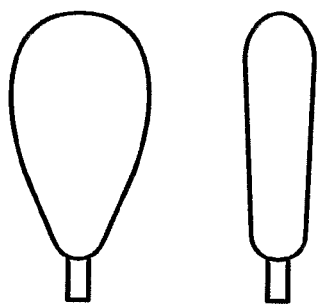

The device of the present invention is positioned between the urinary bladder and sacrum or between the rectum and urinary bladder (see FIG. 7a) with an extension or an additional device in the Douglas pouch through the perineum using trans rectal, trans vaginal ultrasound guidance or CT guidance. An extension of the bladder into the Douglas pouch may be provided to push up the bowels. The folded device and sheath measuring between 2 and 3 mm in diameter are introduced through the introducer sheath and the bladder component is deployed and expanded in a space between the rectum and urinary bladder which is prepared as described above. A elongated bladder of 3 to 10 cm in length, 3 to 5 cm in width and having a variable thickness (when expanded) of 1 cm in the intervesical-rectal space to 5 cm height in the distal Douglas pouch position (see FIGS. 7b-c) is used.

The catheter is then detached and the bladder sealed as described above. Radiation therapy is then administered, patients receive 45 Gy (4500 rad) provided in fractions over 5 weeks with or without the addition of neoadjuvant chemotherapy. Surgery is performed 4-6 weeks following completion of the radiotherapy course. Radiotherapy can also be administered following surgery in an adjuvant setting. In the latter case, the prescribed radiation dose is 50.4 Gy which is provided in 28 fractions.

Example 7

Pulmonary Tumors & Mediastinum Lymphomas

The device of the present invention can also be used during radiation therapy to pulmonary tumors or to lymphomas situated in the mediastinum. In pulmonary tumors, the bladder is preferably positioned between the lung and mediastinum containing: great blood vessels, heart, spine with the spinal cord, and lymphatic vessels and nodes, in order to separate a possible medial tumor from healthy tissues. In lymphomas, the device is preferably positioned between the enlarged lymph nodes situated in the superior mediastinum and the heart and great vessels, spine and lung tissue. The device is preferably positioned under CT guidance. The bladder is preferably 5 to 10 cm in length; 3 to 5 cm in width and 1 to 2 cm in thickness when expanded (see FIGS. 8b-c). A number of smaller sized bladders can also be used to efficiently cover this complex space.

The folded device with its sheath measuring between 2 and 3 mm in diameter are introduced through the introducer sheath and the bladder component is deployed and inflated in the mediastinal space (see FIG. 8a) in the proper orientation.

The catheter is then detached and the bladder sealed as described above. In case of pulmonary tumors radiotherapy is administered as either 45 Gy over 15 sessions up to 70 Gy over 70 sessions over a period between 3 to 10 weeks according to type of tumor and stage. Such radiation therapy is typically administered in combination with chemotherapy. In case of mediastinal lymphomas chemotherapy is administered followed by consolidation radiotherapy at a dose of 36 Gy over 4 to 6 weeks to bulky mediastinal disease.

Example 8

Breast Cancer

Another application may be for radiation treatment of breast cancer. This tumor is the most prevalent tumor in women account for 300.000 new cases in US every year. Most patients undergo lumpectomy. In the majority of cases irradiation is given to the nearby breast tissue and case of tumors situated near the chest wall the thoracic wall and lung receive a significant dose of irradiation.

Figure 9A:
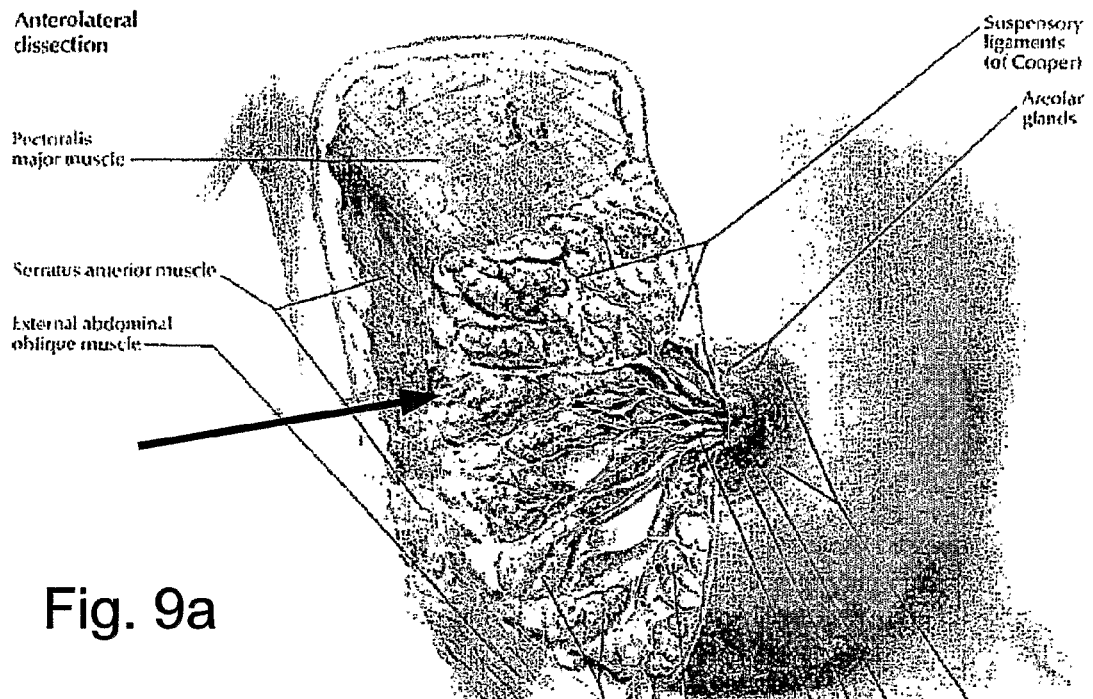
FIGS. 9a-c illustrate breast tissue (FIG. 9a) and an embodiment of the device of the present invention (FIG. 9b—front view.
Figures 9B, 9C:
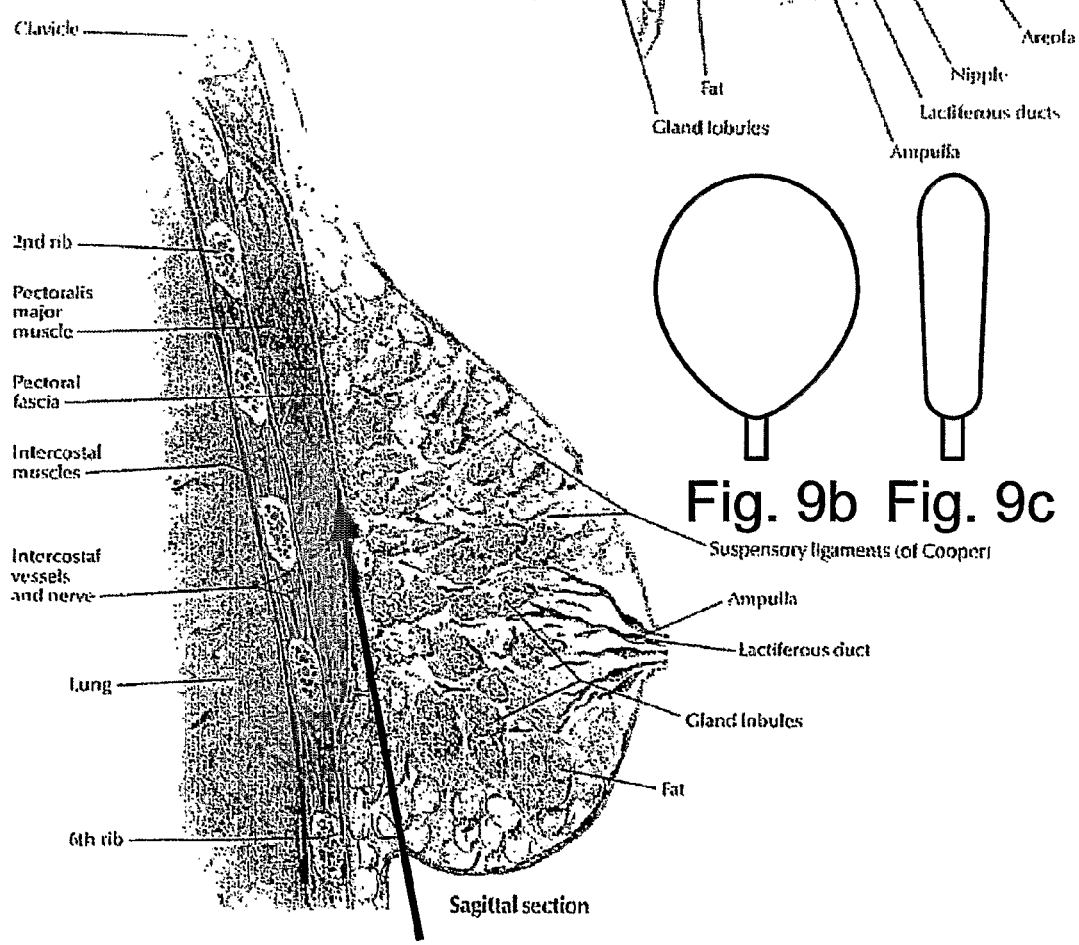

The folded device and sheath measuring between 2 and 5 mm in diameter are introduced through the introducer sheath and the bladder component is deployed and expanded in the space between the breast and abdominal wall (see FIG. 9a). A circular flat bladder 5 to 15 cm in diameter, and 1 to 3 cm in thickness (see FIGS. 9b-c) is preferably used in this procedure.

The catheter is then detached and the bladder sealed as described above. Radiation therapy is then administered. The standard technique of radiotherapy (RT) following breast conserving surgery (BCS) is to treat the entire breast up to a total dose of 45-50 Gy with or without tumor bed boost; typical treatment includes 30 sessions which are administered over a period of six weeks.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of forming a seamless bladder comprising:
   (a) providing a volumetric bladder template produced from material soluble in a first liquid;
   (b) coating said template with a solution of a polymer insoluble in said first liquid to thereby generate a polymeric coat on said template; and
   (c) exposing said template and polymeric coat to said first liquid thereby dissolving said template and leaving said polymeric coat to form the seamless bladder.

2. The method of claim 1, wherein said first liquid is a hydrophilic liquid.

3. The method of claim 1, wherein said material soluble in a first liquid is gelatin or agar.

4. The method of claim 1, wherein said polymer is selected from the group consisting of a poly(alkanoic acid), a polyorhtoester, a polyphosphazene, a polyphosphate ester and a polyanhydride.

5. The method of claim 4, wherein said poly(alkanoic acid) is selected from the group consisting of poly(lactic acid), poly(lactic acid-glycolic acid) and poly(lactic acid-caprolactone).

6. The method of claim 1, wherein coating comprises coating by dipping said template in said first liquid.

7. The method of claim 6, comprising repeating said dipping until a desired thickness is achieved.

8. The method of claim 6, wherein dipping comprises dipping at a constant speed.

9. The method of claim 1, wherein coating comprises coating said template from all sides except for a port region of said bladder.

10. The method of claim 9, comprising forcefully sticking a biodegradable plug into said port.

11. The method of claim 9, comprising removing said dissolved template via said port.

12. The method of claim 1, wherein said bladder is formed to have a port with a diameter of between $1/100$ and $1/5$ of a diameter of said bladder.

13. The method of claim 1, wherein providing a volumetric bladder template comprises forming a bladder template using a mold.

14. The method of claim 1, wherein said polymer is selected to biodegrade when inside a body over a period of weeks to months.

* * * * *